US00PP31060P3

(12) United States Plant Patent
Hansen

(10) Patent No.: US PP31,060 P3
(45) Date of Patent: Nov. 12, 2019

(54) **X *MANGAVE* PLANT NAMED 'WHALE TALE'**

(50) Latin Name: **X *Mangave* times *Agave ovatifolia***
Varietal Denomination: Whale Tale

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 6 days.

(21) Appl. No.: 15/932,526

(22) Filed: Mar. 12, 2018

(65) Prior Publication Data

US 2019/0281745 P1 Sep. 12, 2019

(51) Int. Cl.
*A01H 6/12* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
CPC ..... A01H 6/12; A01H 5/12
See application file for complete search history.

(56) References Cited

PUBLICATIONS

Walters Gardens Catalog 2017-2018.*

* cited by examiner

*Primary Examiner* — Keith O. Robinson

(57) ABSTRACT

A new and unique X *Mangave* plant named 'Whale Tale' characterized by glaucous, silver-grey, slightly-arching, lanceolate foliage with small semi-flexible marginal teeth on deeply-scalloped margins and apical spines. Leaves develop greyed-purple spotting with strong ultraviolet light. The habit is low, wide and slightly arching. Plants are useful for landscaping as specimens or en masse or as container plants in the landscape or in the home.

1 Drawing Sheet

Botanical classification: x *Mangave* times *Agave ovatifolia.*

Variety denomination: 'Whale Tale'.

BACKGROUND OF THE INVENTION

The present invention relates to the new and distinct *Manfreda* x *Agave* hybrid plant, X *Mangave* 'Whale Tale' hybridized by the inventor at a wholesale perennial nursery in Zeeland, Mich., USA as cross between the unreleased proprietary hybrid H10-02-02 (not patented) as the female or seed parent times a selection of *Agave ovatifolia* (not patented) as the male or pollen parent. The female parent, H10-02-02, is a cross of a proprietary selection of *Manfreda maculosa* (not patented) times a proprietary selection of *Agave gypsophila* (not patented). The cross was performed Jun. 18, 2012 and, seeds were harvested and later sown in the fall of 2012. Through trials at the same nursery the plant was originally assigned the breeder code XMANG-12-54-2. The new plant has been successfully asexually propagated by sterile shoot tip tissue culture at the same nursery in Zeeland, Mich. 'Whale Tale' has been found to produce stable and identical plants that maintain all the unique characteristics of the original plant.

No plants of X *Mangave* 'Whale Tale' have been sold, under this or any name, in this country or anywhere in the world, prior to the filing of this application, except to a perennial nursery in Raleigh, N.C. No disclosure of the new plant been made prior to the filing of this application with the exception of that which was disclosed within one year of the filing of this application, and was either derived directly or indirectly from the inventor.

BRIEF SUMMARY OF THE INVENTION

X *Mangave* 'Whale Tale' differs from its parents as well as all other *Manfreda, Agave* and X *Mangave* known to the applicant. Compared with the female parent H10-02-02 the new plant has leaves that are larger, less spotted, with more flexible apical spines, more blue and less wavy. The male parent has leaves that are more ovate, glaucous and less spotted, and the habit is much larger with larger leaves. Further comparison with the female parent is not possible as neither plants nor photographs were maintained. The most similar cultivars known to the inventor are X *Mangave* 'Silver Fox' U.S. Plant Pat. No. 29,642, X *Mangave* 'Catch a Wave' U.S. Plant Pat. No. 29,723, 'Lavender Lady' U.S. Plant Pat. No. 29,194 and co-pending application X *Mangave* 'Mayan Queen' U.S. Plant patent application Ser. No. 15/932,527. 'Silver Fox' has shorter, more upright, more glaucous foliage with greater indentations at the toothed margin. 'Catch a Wave' has more upright habit with broader, more sinuate, more conduplicate, with longer foliage that is slightly less glaucous. 'Lavender Lady' is shorter and more compact in habit with more ovate foliage having more intense purplish markings. 'Mayan Queen' has more greyed-purple spotting on the leaves and more reddish-purple near the base of the foliage. The marginal teeth are also larger and closer together on 'Mayan Queen' than in the new plant.

The new plant, 'Whale Tale', is unique from all of the above cultivars and all *Agave*, X *Mangave* and *Manfreda* known to the inventor by the following combined traits:

1. Low, wide, slightly arching habit;
2. Glaucous, silver-grey foliage develops glaucous covering and irregular greyed-purple spotting with strong ultraviolet light;
3. Moderate growth rate.

BRIEF DESCRIPTION OF THE DRAWINGS

The photographs of x *Mangave* 'Whale Tale'; demonstrate the overall appearance of the new plant including the unique traits of a three-year-old plant grown in a greenhouse in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
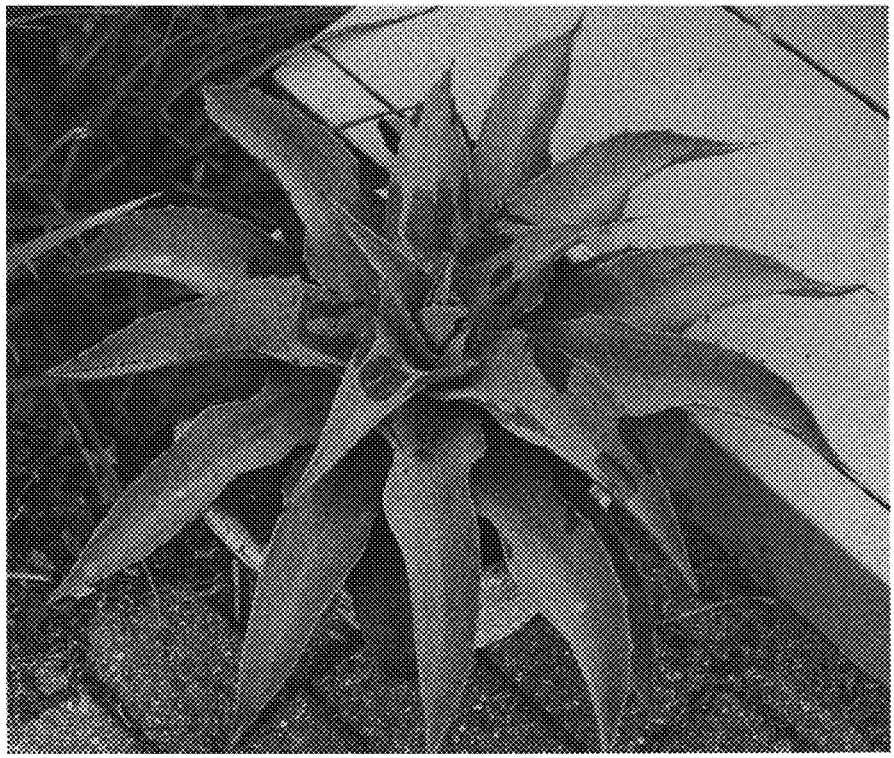
FIG. 1 shows the new plant and foliage from above.
Figure 2:
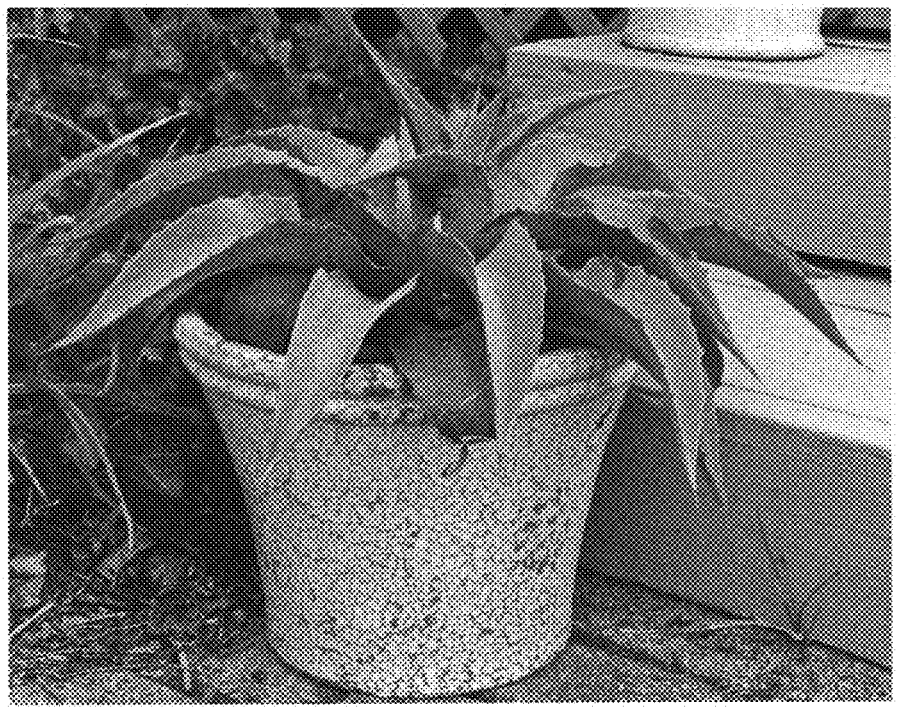
FIG. 2 shows the new plant foliage and habit from a side view.

The following descriptions and color references are based on the 2015 edition of The Royal Horticultural Society Colour Chart except where common dictionary terms are used. The new plant, X *Mangave* 'Whale Tale', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Parentage: Proprietary unreleased hybrid H10-02-02 (not patented) comprising *Manfreda maculosa* x *Agave gypsophila*) as female or seed patent, and an unnamed selection of *Agave ovatifolia* (not patented) as the male or pollen parent;

Propagation: Division of side shoots and sterile shoot-tip tissue culture;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 20 cm long;

Root color: Nearest RHS 158D;

Plant shape and habit: Succulent, herbaceous, freeze-tender perennial with basal rosettes of about 30 leaves radially emerging and outwardly and distally arching from central stem extending below the base of the plant when grown in containers, producing a radially-symmetrical, flat, slightly outwardly mound;

Plant size: Foliage height about 18.0 cm tall from soil line to the top of the leaves and about 52.0 cm wide at the widest point slightly below soil line in container;

Foliage description: Lanceolate; simple; margins scalloped with small firm teeth; apex spinose; base truncate, sessile, clasping; flat to slightly conduplicate; bi-laterally symmetrical;

Leaf size: To about 26.0 cm long, about 5.5 cm wide at base and 5.0 mm thick, average about 24.5 cm long, 4.5 cm wide and 4.5 mm thick; marginal teeth about 1.0 mm long on scalloped indentations about 3.0 mm deep and about 9.0 mm apart; spots average about 2.0 mm across and may connect with intense ultraviolet light;

Foliage fragrance: None observed;

Leaf blade color:

*Adaxial* (*young*).—Blend between nearest RHS 138B and RHS 194B with spots nearest RHS N187A with intense ultraviolet light.

*Abaxial* (*young*).—Blend between nearest RHS 138B and RHS 194C with spots nearest RHS N187B with intense ultraviolet light.

*Adaxial* (*mature*).—Blend between nearest RHS 122C and RHS N189D with spots between RHS N187A and RHS N187B; without glaucous bloom between RHS 146B and RHS 146C.

*Abaxial* (*mature*).—Blend between RHS 122C and RHS N189D.

*Teeth*.—Nearest RHS 167D on young leaves and maturing to nearest RHS 200B.

Apical spine or mucro: Sharp and slightly flexible; average about 4.0 mm long and about 1.0 mm wide at base;

Apical spine or mucro color: Nearest RHS N167D on young expanding leaves and maturing to nearest RHS 200B;

Petiole: Sessile;

Veins: Parallel; not distinct abaxial or adaxial;

Stem: Terete; covered with leaves; about 4.5 cm across and extending to about 3.0 cm above soil; without branching; attitude upwards, erect;

Flowers have not yet been observed.

Fruit and seed have not yet been observed.

Disease resistance: X *Mangave* 'Whale Tale' has not been observed to be resistant to diseases beyond that which is normal for X *Mangave, Agave* or *Manfreda*. The plant is xeromorphic and survives well with minimal water once established. The new plant is hardy at least from USDA zone 9a to 11. Full extent of winter hardiness has not been tested.

It is claimed:

1. A new and distinct cultivar of ornamental X *Mangave* plant named 'Whale Tale' as herein described and illustrated, suitable for the garden or as a potted plant in the garden or home.

* * * * *